US010904653B2

(12) United States Patent
Boesen

(10) Patent No.: US 10,904,653 B2
(45) Date of Patent: *Jan. 26, 2021

(54) MICROPHONE NATURAL SPEECH CAPTURE VOICE DICTATION SYSTEM AND METHOD

(71) Applicant: BRAGI GmbH, Munich (DE)

(72) Inventor: Peter Vincent Boesen, Munich (DE)

(73) Assignee: BRAGI GmbH, Munich (DE)

(*) Notice: Subject to any disclaimer, the term of this patent is extended or adjusted under 35 U.S.C. 154(b) by 21 days.

This patent is subject to a terminal disclaimer.

(21) Appl. No.: 15/946,100

(22) Filed: Apr. 5, 2018

(65) Prior Publication Data

US 2018/0242071 A1    Aug. 23, 2018

Related U.S. Application Data

(63) Continuation of application No. 15/383,809, filed on Dec. 19, 2016, now Pat. No. 9,980,033.

(Continued)

(51) Int. Cl.
*H04R 1/10* (2006.01)
*G10L 15/26* (2006.01)
(Continued)

(52) U.S. Cl.
CPC ........... *H04R 1/1041* (2013.01); *G06F 19/00* (2013.01); *G06F 40/174* (2020.01); *G10L 15/22* (2013.01);
(Continued)

(58) Field of Classification Search
CPC ...... H04R 1/1041; H04R 1/08; H04R 1/1016; H04R 1/1083; H04R 2460/13;
(Continued)

(56) References Cited

U.S. PATENT DOCUMENTS 2,325,590 A    8/1943 Carlisle et al.
2,430,229 A    11/1947 Kelsey
(Continued)

FOREIGN PATENT DOCUMENTS

CN    204244472 U    4/2015
CN    104683519 A    6/2015
(Continued)

OTHER PUBLICATIONS

Stretchgoal—The Carrying Case for the Dash (Feb. 12, 2014).
(Continued)

*Primary Examiner* — Leshui Zhang
(74) *Attorney, Agent, or Firm* — Goodhue, Coleman & Owens, P.C.

(57) ABSTRACT

A system for voice dictation includes an earpiece, the earpiece may include an earpiece housing sized to fit into an external auditory canal of a user and block the external auditory canal, a first microphone operatively connected to the earpiece housing and positioned to be isolated from ambient sound when the earpiece housing is fitted into the external auditory canal, a second microphone operatively connected to earpiece housing and positioned to sound external from the user, and a processor disposed within the earpiece housing and operatively connected to the first microphone and the second microphone. The system may further include a software application executing on a computing device which provides for receiving the first voice audio stream into a first position of a record and receiving the second voice audio stream into a second position of the record.

12 Claims, 7 Drawing Sheets

Related U.S. Application Data

(60) Provisional application No. 62/270,419, filed on Dec. 21, 2015.

(51) Int. Cl.
| | |
|---|---|
| *H04R 1/08* | (2006.01) |
| *G10L 15/22* | (2006.01) |
| *G16H 10/60* | (2018.01) |
| *H04R 5/033* | (2006.01) |
| *G06F 19/00* | (2018.01) |
| *G06F 40/174* | (2020.01) |

(52) U.S. Cl.
CPC ............ *G10L 15/26* (2013.01); *G16H 10/60* (2018.01); *H04R 1/08* (2013.01); *H04R 1/1016* (2013.01); *H04R 1/1083* (2013.01); *H04R 5/0335* (2013.01); *G10L 2015/227* (2013.01); *H04R 2460/13* (2013.01)

(58) Field of Classification Search
CPC ...... H04R 25/00; H04R 25/30; H04R 25/305; H04R 25/35; H04R 25/353; H04R 25/356; H04R 25/50; H04R 25/502; H04R 25/505; H04R 25/402; H04R 25/405; H04R 25/407; H04R 25/43; H04R 25/70; H04R 5/00; H04R 29/004; H04R 29/005; H04R 29/006; H04R 29/008; G06F 17/243; G06F 19/322; G10L 15/22; G10L 15/26; G10L 2015/227
USPC ................ 381/74, 26, 312–331; 340/539.11, 340/539.12; 700/94; 704/270, 270.1, 704/271, 272, 275, 276, 277, 278; 379/93.17, 158, 202.01, 205.01
See application file for complete search history.

(56) References Cited

U.S. PATENT DOCUMENTS

| | | | |
|---|---|---|---|
| 3,047,089 A | 7/1962 | Zwislocki | |
| D208,784 S | 10/1967 | Sanzone | |
| 3,586,794 A | 6/1971 | Michaelis | |
| 3,696,377 A | 10/1972 | Wall | |
| 3,934,100 A | 1/1976 | Harada | |
| 3,983,336 A | 9/1976 | Malek et al. | |
| 4,069,400 A | 1/1978 | Johanson et al. | |
| 4,150,262 A | 4/1979 | Ono | |
| 4,334,315 A | 6/1982 | Ono et al. | |
| D266,271 S | 9/1982 | Johanson et al. | |
| 4,375,016 A | 2/1983 | Harada | |
| 4,588,867 A | 5/1986 | Konomi | |
| 4,617,429 A | 10/1986 | Bellafiore | |
| 4,654,883 A | 3/1987 | Iwata | |
| 4,682,180 A | 7/1987 | Gans | |
| 4,791,673 A | 12/1988 | Schreiber | |
| 4,852,177 A | 7/1989 | Ambrose | |
| 4,865,044 A | 9/1989 | Wallace et al. | |
| 4,984,277 A | 1/1991 | Bisgaard et al. | |
| 5,008,943 A | 4/1991 | Arndt et al. | |
| 5,185,802 A | 2/1993 | Stanton | |
| 5,191,602 A | 3/1993 | Regen et al. | |
| 5,201,007 A | 4/1993 | Ward et al. | |
| 5,201,008 A | 4/1993 | Arndt et al. | |
| D340,286 S | 10/1993 | Seo | |
| 5,280,524 A | 1/1994 | Norris | |
| 5,295,193 A | 3/1994 | Ono | |
| 5,298,692 A | 3/1994 | Ikeda et al. | |
| 5,343,532 A | 8/1994 | Shugart | |
| 5,347,584 A | 9/1994 | Narisawa | |
| 5,363,444 A | 11/1994 | Norris | |
| 5,444,786 A | 8/1995 | Raviv | |
| D367,113 S | 2/1996 | Weeks | |
| 5,497,339 A | 3/1996 | Bernard | |
| 5,606,621 A | 2/1997 | Reiter et al. | |
| 5,613,222 A | 3/1997 | Guenther | |
| 5,654,530 A | 8/1997 | Sauer et al. | |
| 5,692,059 A | 11/1997 | Kruger | |
| 5,721,783 A | 2/1998 | Anderson | |
| 5,748,743 A | 5/1998 | Weeks | |
| 5,749,072 A | 5/1998 | Mazurkiewicz et al. | |
| 5,771,438 A | 6/1998 | Palermo et al. | |
| D397,796 S | 9/1998 | Yabe et al. | |
| 5,802,167 A | 9/1998 | Hong | |
| 5,844,996 A | 12/1998 | Enzmann et al. | |
| D410,008 S | 5/1999 | Almqvist | |
| 5,929,774 A | 7/1999 | Charlton | |
| 5,933,506 A | 8/1999 | Aoki et al. | |
| 5,949,896 A | 9/1999 | Nageno et al. | |
| 5,987,146 A | 11/1999 | Pluvinage et al. | |
| 6,021,207 A | 2/2000 | Puthuff et al. | |
| 6,054,989 A | 4/2000 | Robertson et al. | |
| 6,081,724 A | 6/2000 | Wilson | |
| 6,084,526 A | 7/2000 | Blotky et al. | |
| 6,094,492 A | 7/2000 | Boesen | |
| 6,111,569 A | 8/2000 | Brusky et al. | |
| 6,112,103 A | 8/2000 | Puthuff | |
| 6,157,727 A | 12/2000 | Rueda | |
| 6,167,039 A | 12/2000 | Karlsson et al. | |
| 6,181,801 B1 | 1/2001 | Puthuff et al. | |
| 6,185,152 B1 | 2/2001 | Shen | |
| 6,208,372 B1 | 3/2001 | Barraclough | |
| 6,230,029 B1 | 5/2001 | Yegiazaryan et al. | |
| 6,275,789 B1 | 8/2001 | Moser et al. | |
| 6,339,754 B1 | 1/2002 | Flanagan et al. | |
| D455,835 S | 4/2002 | Anderson et al. | |
| 6,408,081 B1 | 6/2002 | Boesen | |
| 6,424,820 B1 | 7/2002 | Burdick et al. | |
| D464,039 S | 10/2002 | Boesen | |
| 6,470,893 B1 | 10/2002 | Boesen | |
| D468,299 S | 1/2003 | Boesen | |
| D468,300 S | 1/2003 | Boesen | |
| 6,542,721 B2 | 4/2003 | Boesen | |
| 6,560,468 B1 | 5/2003 | Boesen | |
| 6,563,301 B2 | 5/2003 | Gventer | |
| 6,654,721 B2 | 11/2003 | Handelman | |
| 6,664,713 B2 | 12/2003 | Boesen | |
| 6,690,807 B1 | 2/2004 | Meyer | |
| 6,694,180 B1 | 2/2004 | Boesen | |
| 6,718,043 B1 | 4/2004 | Boesen | |
| 6,738,485 B1 | 5/2004 | Boesen | |
| 6,748,095 B1 | 6/2004 | Goss | |
| 6,754,358 B1 | 6/2004 | Boesen et al. | |
| 6,784,873 B1 | 8/2004 | Boesen et al. | |
| 6,823,195 B1 | 11/2004 | Boesen | |
| 6,852,084 B1 | 2/2005 | Boesen | |
| 6,879,698 B2 | 4/2005 | Boesen | |
| 6,892,082 B2 | 5/2005 | Boesen | |
| 6,920,229 B2 | 7/2005 | Boesen | |
| 6,952,483 B2 | 10/2005 | Boesen et al. | |
| 6,987,986 B2 | 1/2006 | Boesen | |
| 7,010,137 B1 | 3/2006 | Leedom et al. | |
| 7,113,611 B2 | 9/2006 | Leedom et al. | |
| D532,520 S | 11/2006 | Kampmeier et al. | |
| 7,136,282 B1 | 11/2006 | Rebeske | |
| 7,203,331 B2 | 4/2007 | Boesen | |
| 7,209,569 B2 | 4/2007 | Boesen | |
| 7,215,790 B2 | 5/2007 | Boesen et al. | |
| D549,222 S | 8/2007 | Huang | |
| D554,756 S | 11/2007 | Sjursen et al. | |
| 7,403,629 B1 | 7/2008 | Aceti et al. | |
| D579,006 S | 10/2008 | Kim et al. | |
| 7,463,902 B2 | 12/2008 | Boesen | |
| 7,508,411 B2 | 3/2009 | Boesen | |
| 7,532,901 B1 | 5/2009 | LaFranchise et al. | |
| D601,134 S | 9/2009 | Elabidi et al. | |
| 7,825,626 B2 | 11/2010 | Kozisek | |
| 7,859,469 B1 | 12/2010 | Rosener et al. | |
| 7,965,855 B1 | 6/2011 | Ham | |
| 7,979,035 B2 | 7/2011 | Griffin et al. | |
| 7,983,628 B2 | 7/2011 | Boesen | |
| D647,491 S | 10/2011 | Chen et al. | |

(56) References Cited

U.S. PATENT DOCUMENTS

| | | |
|---|---|---|
| 8,095,188 B2 | 1/2012 | Shi |
| 8,108,143 B1 | 1/2012 | Tester |
| 8,140,357 B1 | 3/2012 | Boesen |
| D666,581 S | 9/2012 | Perez |
| 8,300,864 B2 | 10/2012 | Müllenborn et al. |
| 8,406,448 B2 | 3/2013 | Lin et al. |
| 8,430,817 B1 | 4/2013 | Al-Ali et al. |
| 8,436,780 B2 | 5/2013 | Schantz et al. |
| D687,021 S | 7/2013 | Yuen |
| 8,679,012 B1 | 3/2014 | Kayyali |
| 8,719,877 B2 | 5/2014 | VonDoenhoff et al. |
| 8,774,434 B2 | 7/2014 | Zhao et al. |
| 8,831,266 B1 | 9/2014 | Huang |
| 8,891,800 B1 | 11/2014 | Shaffer |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,461,403 B2 | 10/2016 | Gao et al. |
| 9,510,159 B1 | 11/2016 | Cuddihy et al. |
| D773,439 S | 12/2016 | Walker |
| D775,158 S | 12/2016 | Dong et al. |
| D777,710 S | 1/2017 | Palmborg et al. |
| 9,544,689 B2 | 1/2017 | Fisher et al. |
| D788,079 S | 5/2017 | Son et al. |
| 9,684,778 B2 | 6/2017 | Tharappel et al. |
| 9,711,062 B2 | 7/2017 | Ellis et al. |
| 9,729,979 B2 | 8/2017 | Özden |
| 9,767,709 B2 | 9/2017 | Ellis |
| 9,848,257 B2 | 12/2017 | Ambrose et al. |
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002039 A1* | 1/2002 | Qureshey ............ G06Q 30/0641 |
| | | 455/344 |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0102931 A1 | 5/2004 | Ellis et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0197063 A1 | 9/2005 | White |
| 2005/0212911 A1 | 9/2005 | Marvit et al. |
| 2005/0251455 A1 | 11/2005 | Boesen |
| 2005/0266876 A1 | 12/2005 | Boesen |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2007/0102009 A1 | 5/2007 | Wong et al. |
| 2007/0239225 A1 | 10/2007 | Saringer |
| 2007/0269785 A1 | 11/2007 | Yamanoi |
| 2008/0076972 A1 | 3/2008 | Dorogusker et al. |
| 2008/0090622 A1 | 4/2008 | Kim et al. |
| 2008/0102424 A1 | 5/2008 | Holljes |
| 2008/0146890 A1 | 6/2008 | LeBoeuf et al. |
| 2008/0187163 A1 | 8/2008 | Goldstein et al. |
| 2008/0215239 A1 | 9/2008 | Lee |
| 2008/0253583 A1* | 10/2008 | Goldstein ............ H04R 1/1091 |
| | | 381/92 |
| 2008/0254780 A1 | 10/2008 | Kuhl et al. |
| 2008/0255430 A1 | 10/2008 | Alexandersson et al. |
| 2008/0298606 A1 | 12/2008 | Johnson et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0041313 A1 | 2/2009 | Brown |
| 2009/0073070 A1 | 3/2009 | Rofougaran |
| 2009/0097689 A1 | 4/2009 | Prest et al. |
| 2009/0105548 A1 | 4/2009 | Bart |
| 2009/0154739 A1 | 6/2009 | Zellner |
| 2009/0191920 A1 | 7/2009 | Regen et al. |
| 2009/0226017 A1 | 9/2009 | Abolfathi et al. |
| 2009/0240947 A1 | 9/2009 | Goyal et al. |
| 2009/0245559 A1 | 10/2009 | Boltyenkov et al. |
| 2009/0261114 A1 | 10/2009 | McGuire et al. |
| 2009/0296968 A1 | 12/2009 | Wu et al. |
| 2009/0303073 A1 | 12/2009 | Gilling et al. |
| 2009/0304210 A1 | 12/2009 | Weisman |
| 2010/0033313 A1 | 2/2010 | Keady et al. |
| 2010/0075631 A1* | 3/2010 | Black ..................... H04W 4/80 |
| | | 455/410 |
| 2010/0166206 A1 | 7/2010 | Macours |
| 2010/0203831 A1 | 8/2010 | Muth |
| 2010/0210212 A1 | 8/2010 | Sato |
| 2010/0290636 A1 | 11/2010 | Mao et al. |
| 2010/0320961 A1 | 12/2010 | Castillo et al. |
| 2011/0018731 A1 | 1/2011 | Linsky et al. |
| 2011/0103609 A1 | 5/2011 | Pelland et al. |
| 2011/0137141 A1 | 6/2011 | Razoumov et al. |
| 2011/0140844 A1 | 6/2011 | McGuire et al. |
| 2011/0239497 A1 | 10/2011 | McGuire et al. |
| 2011/0286615 A1 | 11/2011 | Olodort et al. |
| 2011/0293105 A1 | 12/2011 | Arie et al. |
| 2012/0057740 A1 | 3/2012 | Rosal |
| 2012/0155670 A1 | 6/2012 | Rutschman |
| 2012/0159617 A1 | 6/2012 | Wu et al. |
| 2012/0163626 A1 | 6/2012 | Booij et al. |
| 2012/0197737 A1 | 8/2012 | LeBoeuf et al. |
| 2012/0235883 A1 | 9/2012 | Border et al. |
| 2012/0309453 A1 | 12/2012 | Maguire |
| 2013/0106454 A1 | 5/2013 | Liu et al. |
| 2013/0154826 A1 | 6/2013 | Ratajczyk |
| 2013/0178967 A1 | 7/2013 | Mentz |
| 2013/0200999 A1 | 8/2013 | Spodak et al. |
| 2013/0204617 A1 | 8/2013 | Kuo et al. |
| 2013/0293494 A1 | 11/2013 | Reshef |
| 2013/0316642 A1 | 11/2013 | Newham |
| 2013/0346168 A1 | 12/2013 | Zhou et al. |
| 2014/0004912 A1 | 1/2014 | Rajakarunanayake |
| 2014/0014697 A1 | 1/2014 | Schmierer et al. |
| 2014/0020089 A1 | 1/2014 | Perini, II |
| 2014/0072136 A1 | 3/2014 | Tenenbaum et al. |
| 2014/0072146 A1 | 3/2014 | Itkin et al. |
| 2014/0073429 A1 | 3/2014 | Meneses et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0146973 A1 | 5/2014 | Liu et al. |
| 2014/0153768 A1 | 6/2014 | Hagen et al. |
| 2014/0163771 A1 | 6/2014 | Demeniuk |
| 2014/0185828 A1 | 7/2014 | Helbling |
| 2014/0219467 A1 | 8/2014 | Kurtz |
| 2014/0222462 A1 | 8/2014 | Shakil et al. |
| 2014/0235169 A1 | 8/2014 | Parkinson et al. |
| 2014/0270227 A1 | 9/2014 | Swanson |
| 2014/0270271 A1 | 9/2014 | Dehe et al. |
| 2014/0276227 A1 | 9/2014 | Pérez |

(56) References Cited

U.S. PATENT DOCUMENTS

| | | |
|---|---|---|
| 2014/0310595 A1 | 10/2014 | Acharya et al. |
| 2014/0321682 A1 | 10/2014 | Kofod-Hansen et al. |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0035643 A1 | 2/2015 | Kursun |
| 2015/0036835 A1 | 2/2015 | Chen |
| 2015/0056584 A1 | 2/2015 | Boulware et al. |
| 2015/0110587 A1 | 4/2015 | Hori |
| 2015/0148989 A1 | 5/2015 | Cooper et al. |
| 2015/0181356 A1 | 6/2015 | Krystek et al. |
| 2015/0230022 A1 | 8/2015 | Sakai et al. |
| 2015/0245127 A1 | 8/2015 | Shaffer |
| 2015/0256949 A1 | 9/2015 | Vanpoucke et al. |
| 2015/0264472 A1 | 9/2015 | Aase |
| 2015/0264501 A1 | 9/2015 | Hu et al. |
| 2015/0317565 A1 | 11/2015 | Li et al. |
| 2015/0358751 A1 | 12/2015 | Deng et al. |
| 2015/0359436 A1 | 12/2015 | Shim et al. |
| 2015/0364058 A1 | 12/2015 | Lagree et al. |
| 2015/0373467 A1 | 12/2015 | Gelter |
| 2015/0373474 A1 | 12/2015 | Kraft et al. |
| 2015/0379251 A1 | 12/2015 | Komaki |
| 2016/0033280 A1 | 2/2016 | Moore et al. |
| 2016/0034249 A1 | 2/2016 | Lee et al. |
| 2016/0071526 A1* | 3/2016 | Wingate .................. G01S 3/802 704/233 |
| 2016/0072558 A1 | 3/2016 | Hirsch et al. |
| 2016/0073189 A1 | 3/2016 | Lindén et al. |
| 2016/0094550 A1 | 3/2016 | Bradley et al. |
| 2016/0100262 A1 | 4/2016 | Inagaki |
| 2016/0119737 A1 | 4/2016 | Mehnert et al. |
| 2016/0124707 A1 | 5/2016 | Ermilov et al. |
| 2016/0125892 A1 | 5/2016 | Bowen et al. |
| 2016/0140870 A1 | 5/2016 | Connor |
| 2016/0142818 A1 | 5/2016 | Park |
| 2016/0162259 A1 | 6/2016 | Zhao et al. |
| 2016/0209691 A1 | 7/2016 | Yang et al. |
| 2016/0253994 A1 | 9/2016 | Panchapagesan et al. |
| 2016/0324478 A1* | 11/2016 | Goldstein .............. A61B 5/721 |
| 2016/0353196 A1 | 12/2016 | Baker et al. |
| 2016/0360350 A1 | 12/2016 | Watson et al. |
| 2017/0021257 A1 | 1/2017 | Gilbert et al. |
| 2017/0046503 A1 | 2/2017 | Cho et al. |
| 2017/0059152 A1 | 3/2017 | Hirsch et al. |
| 2017/0060262 A1 | 3/2017 | Hviid et al. |
| 2017/0060269 A1 | 3/2017 | Forstner et al. |
| 2017/0061751 A1 | 3/2017 | Loermann et al. |
| 2017/0061817 A1 | 3/2017 | Mettler |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1 | 3/2017 | Hviid et al. |
| 2017/0064437 A1 | 3/2017 | Hviid et al. |
| 2017/0078780 A1 | 3/2017 | Qian et al. |
| 2017/0078785 A1 | 3/2017 | Qian et al. |
| 2017/0100277 A1 | 4/2017 | Ke |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0127168 A1 | 5/2017 | Briggs et al. |
| 2017/0131094 A1 | 5/2017 | Kulik |
| 2017/0142511 A1 | 5/2017 | Dennis |
| 2017/0146801 A1 | 5/2017 | Stempora |
| 2017/0150920 A1 | 6/2017 | Chang et al. |
| 2017/0151085 A1 | 6/2017 | Chang et al. |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0164890 A1 | 6/2017 | Leip et al. |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0188127 A1 | 6/2017 | Perianu et al. |
| 2017/0188132 A1 | 6/2017 | Hirsch et al. |
| 2017/0193978 A1 | 7/2017 | Goldman |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0251933 A1 | 9/2017 | Braun et al. |
| 2017/0257698 A1 | 9/2017 | Boesen et al. |
| 2017/0258329 A1 | 9/2017 | Marsh |
| 2017/0263236 A1 | 9/2017 | Boesen et al. |
| 2017/0263376 A1 | 9/2017 | Verschueren et al. |
| 2017/0266494 A1 | 9/2017 | Crankson et al. |
| 2017/0273622 A1 | 9/2017 | Boesen |
| 2017/0280257 A1 | 9/2017 | Gordon et al. |
| 2017/0301337 A1 | 10/2017 | Golani et al. |
| 2017/0361213 A1 | 12/2017 | Goslin et al. |
| 2017/0366233 A1 | 12/2017 | Hviid et al. |
| 2018/0007994 A1 | 1/2018 | Boesen et al. |
| 2018/0008194 A1 | 1/2018 | Boesen |
| 2018/0008198 A1 | 1/2018 | Kingscott |
| 2018/0009447 A1 | 1/2018 | Boesen et al. |
| 2018/0011006 A1 | 1/2018 | Kingscott |
| 2018/0011682 A1 | 1/2018 | Milevski et al. |
| 2018/0011994 A1 | 1/2018 | Boesen |
| 2018/0012228 A1 | 1/2018 | Milevski et al. |
| 2018/0013195 A1 | 1/2018 | Hviid et al. |
| 2018/0014102 A1 | 1/2018 | Hirsch et al. |
| 2018/0014103 A1 | 1/2018 | Martin et al. |
| 2018/0014104 A1 | 1/2018 | Boesen et al. |
| 2018/0014107 A1 | 1/2018 | Razouane et al. |
| 2018/0014108 A1 | 1/2018 | Dragicevic et al. |
| 2018/0014109 A1 | 1/2018 | Boesen |
| 2018/0014113 A1 | 1/2018 | Boesen |
| 2018/0014140 A1 | 1/2018 | Milevski et al. |
| 2018/0014436 A1 | 1/2018 | Milevski |
| 2018/0034951 A1 | 2/2018 | Boesen |
| 2018/0040093 A1 | 2/2018 | Boesen |
| 2018/0042501 A1 | 2/2018 | Adi et al. |

FOREIGN PATENT DOCUMENTS

| | | |
|---|---|---|
| CN | 104837094 A | 8/2015 |
| EP | 1469659 A1 | 10/2004 |
| EP | 1017252 A3 | 5/2006 |
| EP | 2903186 A1 | 8/2015 |
| GB | 2074817 | 4/1981 |
| GB | 2508226 A | 5/2014 |
| JP | 06292195 | 10/1998 |
| WO | 2008103925 A1 | 8/2008 |
| WO | 2008113053 A1 | 9/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014046602 A1 | 3/2014 |
| WO | 2014043179 A3 | 7/2014 |
| WO | 2015061633 A2 | 4/2015 |
| WO | 2015110577 A1 | 7/2015 |
| WO | 2015110587 A1 | 7/2015 |

(56) References Cited

FOREIGN PATENT DOCUMENTS

| | | |
|---|---|---|
| WO | 2016032990 A1 | 3/2016 |
| WO | 2016187869 A1 | 12/2016 |

OTHER PUBLICATIONS

Stretchgoal—Windows Phone Support (Feb. 17, 2014).
The Dash + The Charging Case & The BRAGI News (Feb. 21, 2014).
The Dash-A Word From Our Software, Mechanical and Acoustics Team + An Update (Mar. 11, 2014).
Update From BRAGI—$3,000,000—Yipee (Mar. 22, 2014).
Weisiger; "Conjugated Hyperbilirubinemia", Jan. 5, 2016.
Wertzner et al., "Analysis of fundamental frequency, jitter, shimmer and vocal intensity in children with phonological disorders", V. 71, n.5, 582-588, Sep./Oct. 2005; Brazilian Journal of Othrhinolaryngology.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).
Wikipedia, "Wii Balance Board", "https://en.wikipedia.org/wiki/Wii_Balance_Board", 3 pages, (Jul. 20, 2017).
Akkermans, "Acoustic Ear Recognition for Person Identification", Automatic Identification Advanced Technologies, 2005 pp. 219-223.
Alzahrani et al: "A Multi-Channel Opto-Electronic Sensor to Accurately Monitor Heart Rate against Motion Artefact during Exercise", Sensors, vol. 15, No. 10, Oct. 12, 2015, pp. 25681-25702, XPO55334602, DOI: 10.3390/s151025681 the whole document.
Announcing the $3,333,333 Stretch Goal (Feb. 24, 2014).
Ben Coxworth: "Graphene-based ink could enable low-cost, foldable electronics", "Journal of Physical Chemistry Letters", Northwestern University, (May 22, 2013).
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
BRAGI is on Facebook (2014).
BRAGI Update—Arrival of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, A Lot to Be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing—Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, on Track(May 16, 2015).
BRAGI Update—Beta2 Production and Factory Line(Aug. 20, 2015).
BRAGI Update—Certifications, Production, Ramping Up.
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 21, 2015).
BRAGI Update—Getting Close(Aug. 6, 2015).
BRAGI Update—On Track, Design Verification, How It Works and What's Next(Jul. 15, 2015).
BRAGI Update—On Track, On Track and Gems Overview.
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Healthcare Risk Management Review, "Nuance updates computer-assisted physician documentation solution" (Oct. 20, 2016).
Hoffman, "How to Use Android Beam to Wirelessly Transfer Content Between Devices", (Feb. 22, 2013).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces A Health + Mobility Concept for Wellness in Mobility", Fountain Valley, Californa (2017).
International Search Report & Written Opinion, PCT/EP16/70245 (dated Nov. 16, 2016).
International Search Report & Written Opinion, PCT/EP2016/070231 (dated Nov. 18, 2016).
International Search Report & Written Opinion, PCT/EP2016/070247 (dated Nov. 18, 2016).
International Search Report & Written Opinion, PCT/EP2016/07216 (dated Oct. 18, 2016).
International Search Report and Written Opinion, PCT/EP2016/070228 (dated Jan. 9, 2017).
Jain A et al: "Score normalization in multimodal biometric systems", Pattern Recognition, Elsevier, GB, vol. 38, No. 12, Dec. 31, 2005, pp. 2270-2285, XPO27610849, ISSN: 0031-3203.
Last Push Before the Kickstarter Campaign Ends on Monday 4pm CET (Mar. 28, 2014).
Lovejoy: "Touch ID built into iPhone display one step closer as third-party company announces new tech", "http://9to5mac.com/2015/07/21/virtualhomebutton/" (Jul. 21, 2015).
Nemanja Paunovic et al, "A methodology for testing complex professional electronic systems", Serbian Journal of Electrical Engineering, vol. 9, No. 1, Feb. 1, 2012, pp. 71-80, XPO55317584, YU.
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Nuance, "ING Netherlands Launches Voice Biometrics Payment System in the Mobile Banking App Powered by Nuance", "https://www.nuance.com/about-us/newsroom/press-releases/ing-netherlands-launches-nuance-voice-biometirics.html", 4 pages (Jul. 28, 2015).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).

* cited by examiner

MICROPHONE NATURAL SPEECH CAPTURE VOICE DICTATION SYSTEM AND METHOD

PRIORITY STATEMENT

This application claims priority to U.S. Provisional Patent Application No. 62/270,419 filed on Dec. 21, 2015 titled Microphone Natural Capture Voice Dictation System and Method and is a continuation of U.S. patent application Ser. No. 15/383,809 filed on Dec. 19, 2016 titled Microphone Natural Speech Capture Voice Dictation System and Method all of which are hereby incorporated by reference in their entireties.

FIELD OF THE INVENTION

The present invention relates to wearable devices. More particularly, but not exclusively, the present invention relates to ear pieces.

BACKGROUND

The patient medical record is the essential document of the medical profession which accurately and adequately captures the details of each patient encounter. Over the years, the requirements of the document have changed, as electronic medical records have added significant new levels of data required for processing. Such new burdens have significant impact on the health care providers, both personally and professionally. On a professional level, these new demands require protracted lengths of time to fulfill the demands of documentation. Additionally, these demands require health care professionals to spend an increasing segment of their time documenting the patient visit. This removes them from what they are trained to do: patient care. On a personal level, such increasing demands are the source of frustration, fatigue and increasing dissatisfaction. Therefore, what is needed is a new system that effectively captures critical data for the documentation process at the point of service.

SUMMARY

Therefore, it is a primary object, feature, or advantage of the present invention to improve over the state of the art.

It is a further object, feature, or advantage of the present invention to provide for accurate accuracy in the voice capture of a user of a wearable device.

It is a still further object, feature, or advantage of the present invention to markedly improve data capture from a wearable user due to isolation of the bone microphone.

Another object, feature, or advantage is to acquire patient voice signals in real time, using an external facing microphone to detect patient voice inputs.

Yet another object, feature, or advantage is to allow for instantaneous voice to text conversion.

A further object, feature, or advantage is to allow for capture of a voice snippet at a position within a document.

A still further object, feature, or advantage to allow for editing and correction of incorrect segments of the voice to text conversion.

Another object, feature, or advantage is to allow for standard edits to other non-voice sections of a document.

Yet another object, feature, or advantage is to allow for insertion of voice to text snippets at the direction of the primary user, in this case the health care provider.

A further object, feature, or advantage is to allow for the capture of the patient encounter at the point of service, greatly improving accuracy while simultaneously saving time and money.

A still further object, feature, or advantage is to reduce healthcare administrative costs.

Yet another object, feature, or advantage is to collect contextual sensor data at an earpiece.

A further object, feature, or advantage is to create a record and/or interpret nonverbal information as a part of a transcript of a communication.

One or more of these and/or other objects, features, or advantages of the present invention will become apparent from the specification and claims that follow. No single embodiment need provide every object, feature, or advantage. Different embodiments may have different objects, features, or advantages. Therefore, the present invention is not to be limited to or by any objects, features, or advantages stated herein.

A new and novel way of capturing patient information at the point of service is provided. Such a system may be able to distinguish between a physician voice and a patient's voice. The system may use a combination of microphones. The first microphone may be in the external auditory canal of the healthcare provider. It may be optimized to pick up the "Self-voice" of the healthcare provider. This has the distinct advantage of being acoustically isolated in the external canal of the healthcare provider while providing the optimal environment for capturing the "self-voice" of the primary user. The external microphone may be optimized to pick up the vocal sounds from the patient in the room. In doing so, the healthcare user's microphone would be able to discern the difference between the two voices based upon microphone inputs. This allows the optimized speech engine to segregate the two voice inputs. Such inputs can then be directly inputted into the patient record, stored in the selected position within the record as a voice file, or both. In this fashion, the system may provide the ultimate in flexibility to rapidly and accurate capture the conversation between a healthcare worker and patient, convert to text while at the same time allowing for review or modification as needed. Such editing capability allows the user to have the ability to edit all aspects of the document before their electronic signature.

According to one aspect, a system for voice dictation is provided. The system includes an earpiece. The earpiece includes an earpiece housing sized to fit into an external auditory canal of a user and block the external auditory canal, a first microphone operatively connected to the earpiece housing and positioned to be isolated from ambient sound when the earpiece housing is fitted into the external auditory canal, a second microphone operatively connected to earpiece housing and positioned to sound external from the user, and a processor disposed within the earpiece housing and operatively connected to the first microphone and the second microphone. The processor is adapted to capture a first voice audio stream using at least the first microphone, the first voice audio stream associated with the user, and a second voice audio stream using at least the second microphone, the second voice audio stream associated with a person other than the user. The system may also include a software application executing on a computing device which provides for receiving the first voice audio stream into a first position of a record and receiving the second voice audio stream into a second position of the record.

According to another aspect, a method for voice dictation is provided. The method includes providing an earpiece, the earpiece having an earpiece housing sized to fit into an external auditory canal of a user and block the external auditory canal, a first microphone operatively connected to the earpiece housing and positioned to be isolated from ambient sound when the earpiece housing is fitted into the external auditory canal, a second microphone operatively connected to earpiece housing and positioned to sound external from the user; and a processor disposed within the earpiece housing and operatively connected to the first microphone and the second microphone. The processor is adapted to capture a first voice audio stream using at least the first microphone, the first voice audio stream associated with the user, and a second voice audio stream using at least the second microphone, the second voice audio stream associated with a person other than the user. The method further includes capturing a first voice audio stream using at least the first microphone, the first voice audio stream associated with the user, storing the first voice audio stream on a machine readable storage medium, converting the first voice audio stream to text, placing the text within a first form field in a software application, and providing access to the first voice audio stream through the software application.

DETAILED DESCRIPTION

Figure 1:
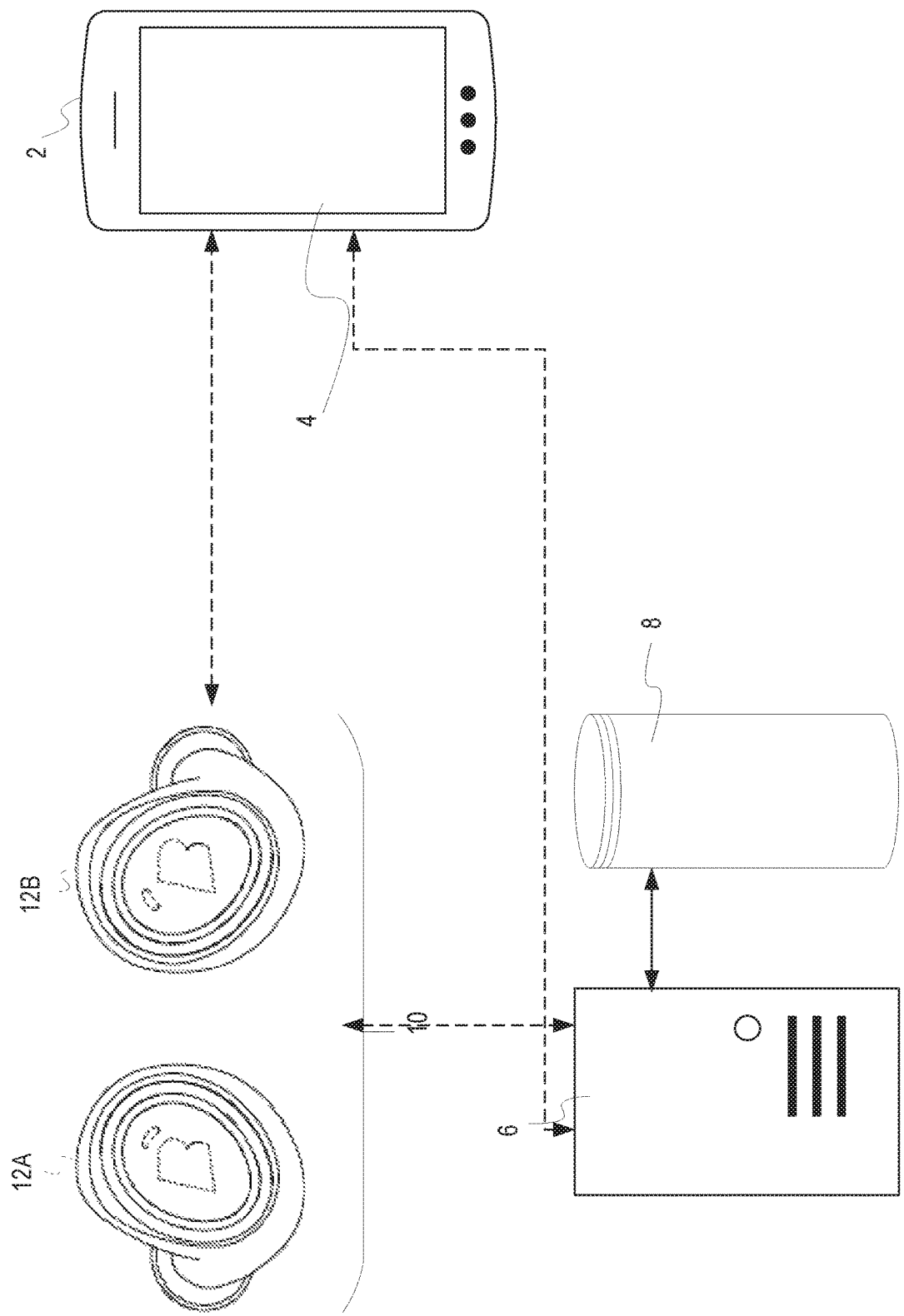
FIG. 1 illustrates one example of a system.

FIG. 1 illustrates one example of a system. As shown in FIG. 1 there are one or more earpieces 10 such as a left earpiece 12A and a right earpiece 12B. Although multiple earpieces are shown, only a single earpiece may be used. The earpieces 12A, 12B may be in operative communication with a computing device 2. The computing device 2 may be a computer, a mobile device such as a phone or tablet, or other type of computing device. There may be a display 4 associated with the computing device 2. A server 6 is also shown. The server 6 is in operative communication with a data store 8 such as a database. The server 6 may be a cloud-based server, a physical server, a virtual server executing on a hardware platform, or other type of server.

Figure 2:
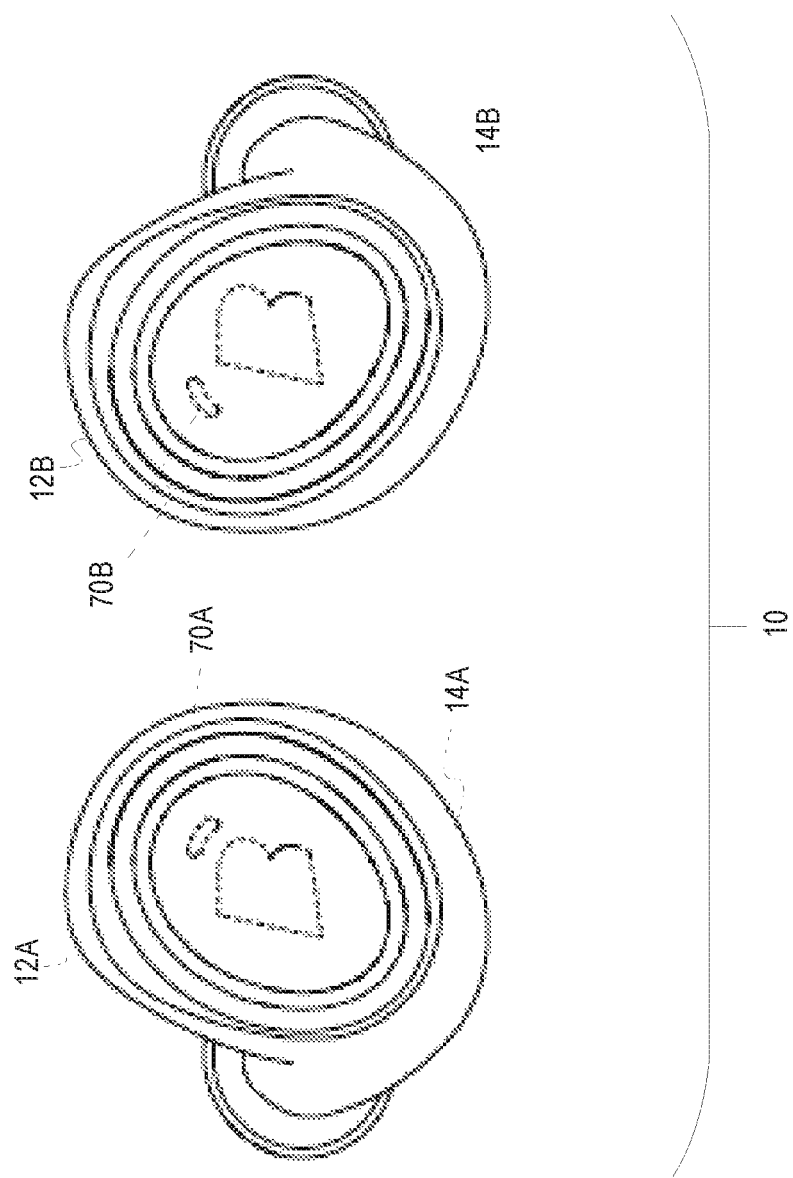
FIG. 2 illustrates a set of earpieces in greater detail.

FIG. 2 illustrates a set of earpieces 10 in greater detail. A left earpiece 12A is housed within an earpiece housing 14A. The left earpiece 12A includes an outward facing microphone 70A. The right earpiece 12B is housed within an earpiece housing 14B. The right earpiece 12B includes an outward facing microphone 70B. The earpieces may be the earpieces which are commercially available from Bragi GmbH such as THE DASH.

Figure 3:
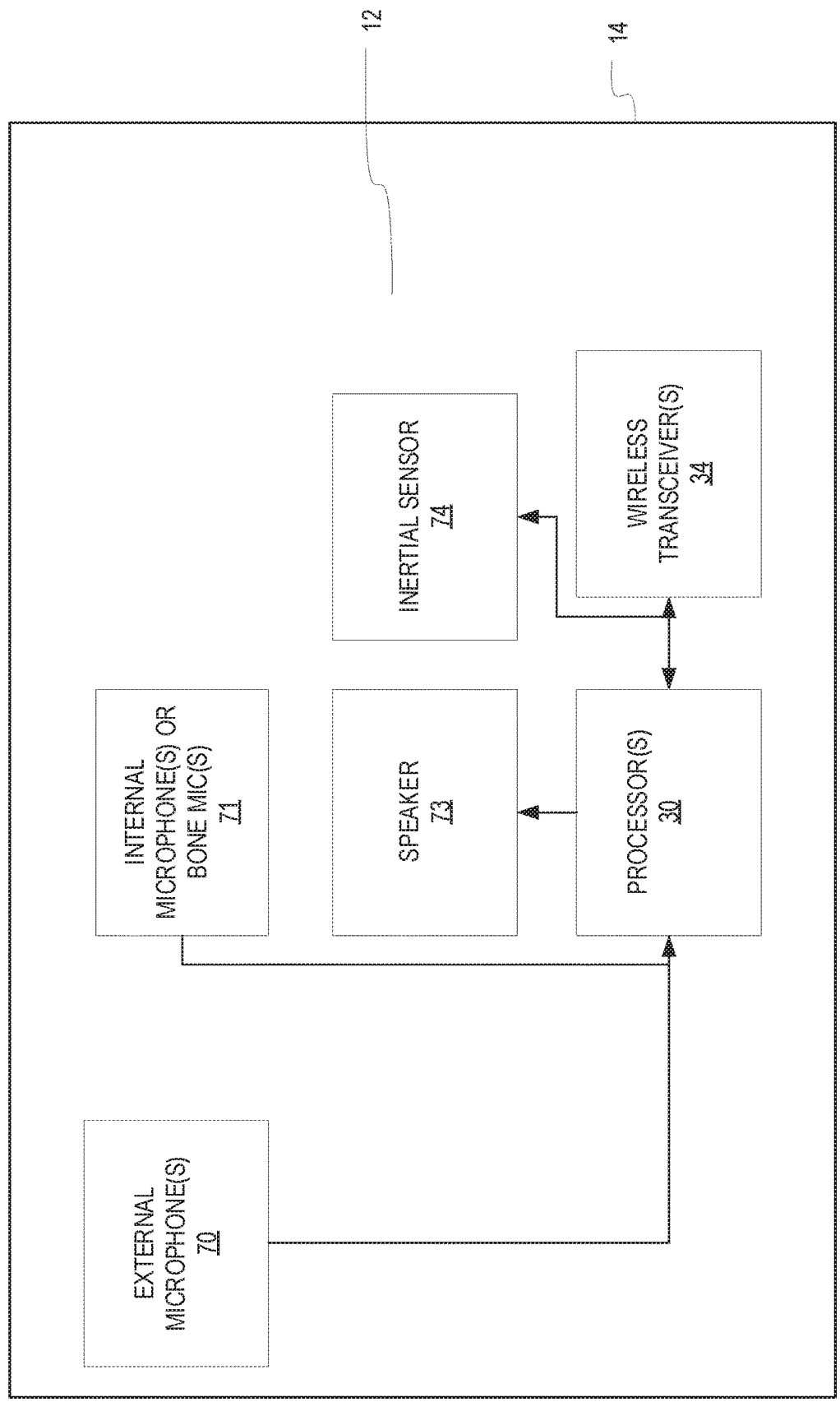
FIG. 3 illustrates a block diagram of one of the earpieces.

FIG. 3 illustrates a block diagram of one of the earpieces 12. The earpiece 12 has an earpiece housing 14. Disposed within the earpiece housing is at least one processor 30. The processor 30 is operatively connected to at least one wireless transceiver 34 which may include a radio transceiver capable of communications using Bluetooth, BLE, Wi-Fi, or other type of radio communication. One or more external microphones 70 and one or more internal microphones 71 are also operatively connected to the processor 30. In addition, a speaker 73 is operatively connected to the processor 30. Note that the external microphone(s) 70 may be positioned to detect or capture voice streams associated with one or more speakers other than the person wearing the earpiece (the user). The one or more internal microphones 71 may be, for example, positioned at or near the external auditory canal or mastoid bone of the user and may provide for picking-up bone vibrations or are otherwise configured to pick up frequency ranges associated with the person wearing the earpiece. In addition, there may be one or more inertial sensors 74 present in the earpiece 12. The inertial sensor may include a gyroscope, accelerometer, or magnetometer. For example, the inertial sensor 74 may be a 9-axis accelerometer which includes a 3-axis gyroscope, a 3-axis accelerometer, and a 3-axis magnetometer.

Figure 4:
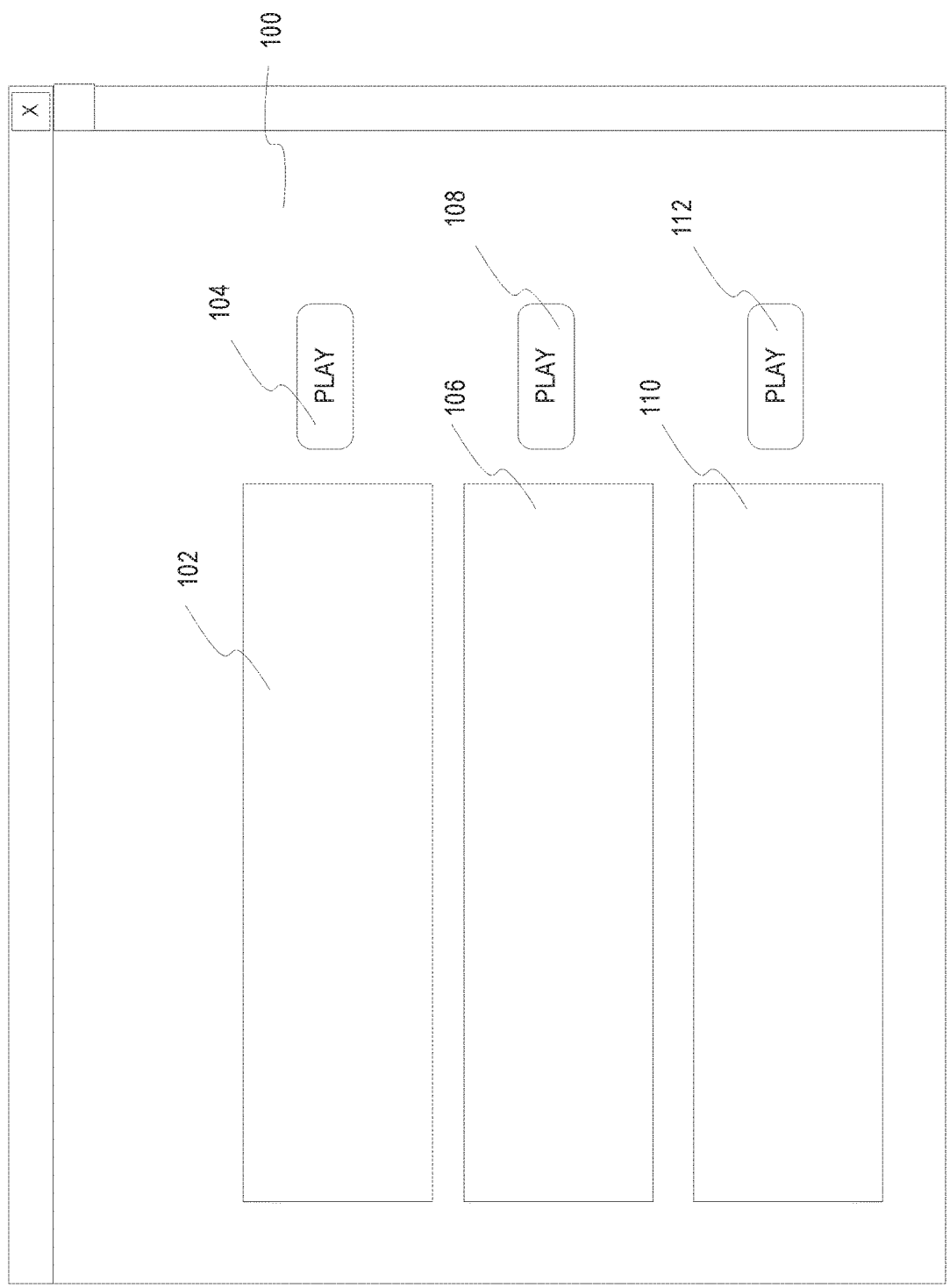
FIG. 4 illustrates one example of a screen display from a software application.

FIG. 4 illustrates one example of a software application which includes a screen display 100. Various form fields 102, 106, 110 are shown. In one embodiment, each time a different speaker (e.g. person) speaks, the software application moves to the next form field. Each form field is populated with text acquired from conversion of voice information to text information. In addition, to this representation of the translated text, the underlying voice stream or voice recording may be played by selecting the corresponding play button 104, 108, 112. Thus, information from multiple individuals may be collected. It is of further note, where the earpiece includes separate microphones for external users and the user of the ear pieces, that separate voice streams may be captured even when the user of the earpieces and another individual are talking at the same time. It is to be further contemplated that there may be more one other individual who is speaking who is within the environment of the user.

Capturing and storing the voice streams or voice snippets and associating these voice streams or voice snippets with the text may provide additional advantages. There is a complete record so that if need be the text information may be correctly later or date if it does not accurately match the voice snippet.

Figure 5:
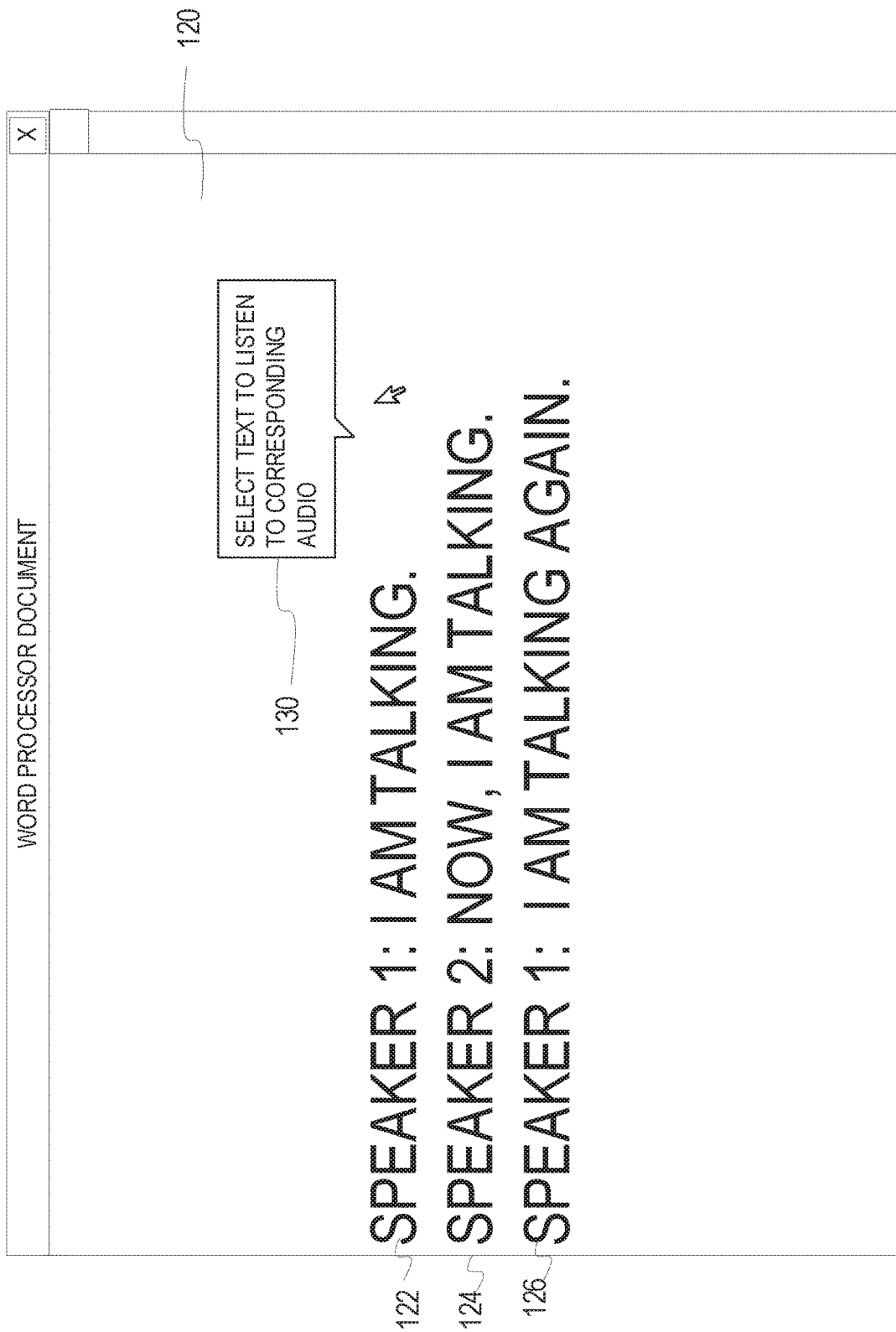
FIG. 5 illustrates one example of a screen display from a word processor.

FIG. 5 illustrates another example of a software application that may be used. As shown in FIG. 5, there is a screen display 120 which may be associated with a word processor document. The word processor may be a word processor such as Microsoft Word, the Microsoft Office Online version of Microsoft Word, WordPerfect, TextMaker, Pages from Apple, Corel Write, Google Docs, or any other word processor. The word processor software may execute on a local machine or on a remote machine such as available through cloud or web access. Functionality may be built-into the word processor or may be provided as an add-in, as a connected application, or otherwise.

As shown in FIG. 5, a transcript may be created which includes text from multiple different speakers. As shown, each speaker may be identified such as "Speaker 1", "Speaker 2." Alternatively, each speaker may be given a name. Also, instead of or in addition to identifying speakers in this fashion, text associated with different speakers may be presented in different colors of text, different fonts, or different styles. As shown in FIG. 5, an icon may be shown associated with a mouse or other control device. The mouse or other control device may be used to select a portion of the text. When that portion of the text is selected, the corresponding audio may be played. Thus, if there appears to be a transcription error in the text, a user may confirm whether there was a transcription error or not. Alternatively, a portion of text may be otherwise selected such as by selecting an icon associated with that portion of the text. Thus, as shown a first speaker may make a first statement 122, a second speaker may make a second statement 124, and the first speaker may make a third statement 126. A tooltip 130 is shown indicating that a user can choose to select text to listen to corresponding audio.

Figure 6:
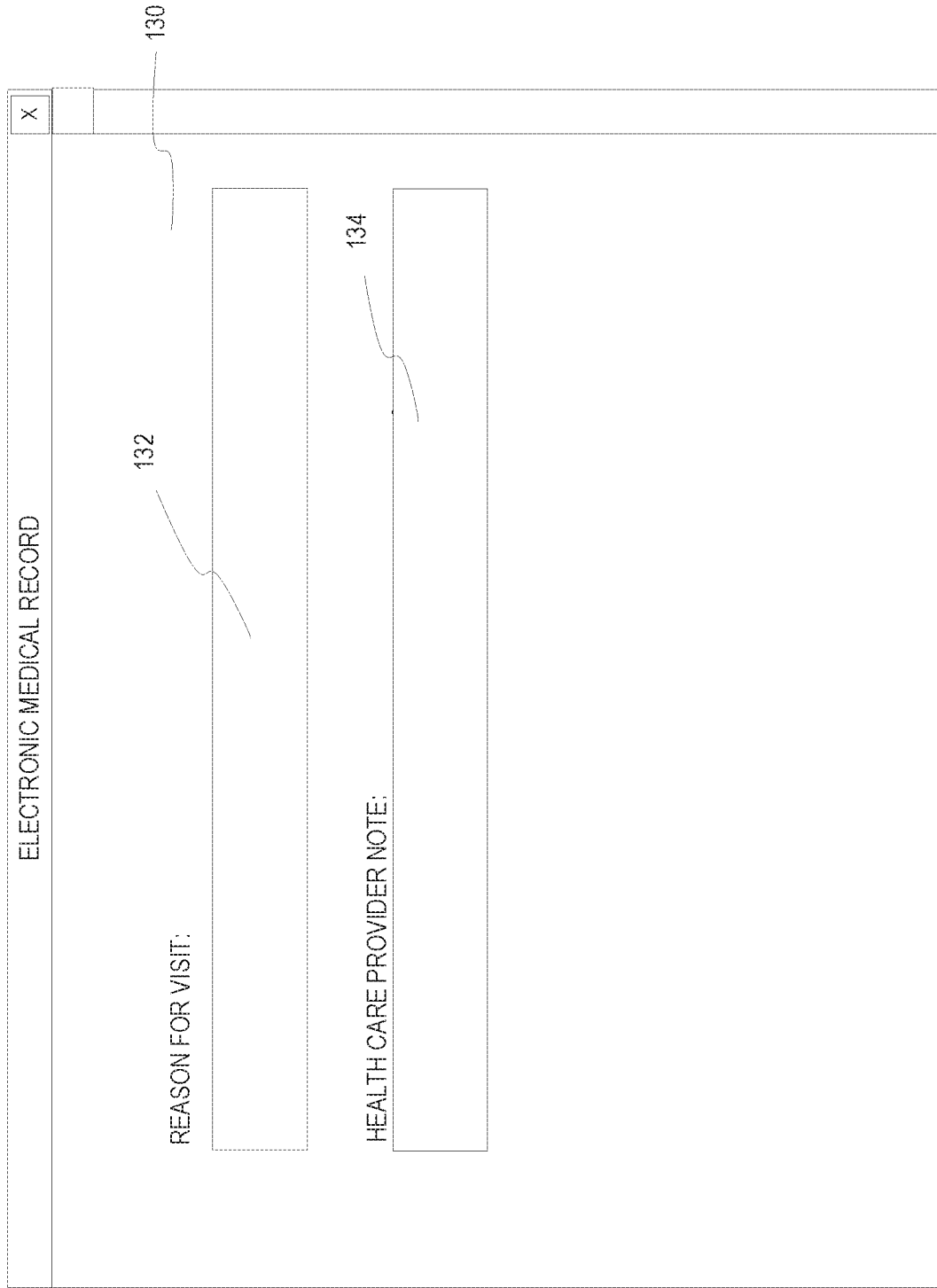
FIG. 6 illustrates one example of a screen display from a medical record application.

FIG. 6 illustrates another example of a software application. FIG. 6 illustrates a screen display 130 associated with an electronic medical record (EMR), electronic health record (EHR), electronic patient record (EPR), or other type of medical record. In the context of a medical record, it is contemplated that information entered into a medical record may come from words dictated by a health care provider or from information obtained orally from a patient. The earpiece described herein may be used to collect audio from both the health care provider (such as by using a bone conduction microphone) and from the patient (such as by using an external facing microphone). For example, as shown in FIG. 6 voice information associated with the reason for the visit, as spoken by a patient, may be input as text into form field 132 and a recording of the audio may be associated with this form field. In addition, voice information, as spoken by the health care provider, may be input as text into form field 134 and a recording of the audio may be associated with this form field. Although given as an example in the context of the medical field, any number of other situations may be appropriate where a transcript of an encounter is desired.

Figure 7:
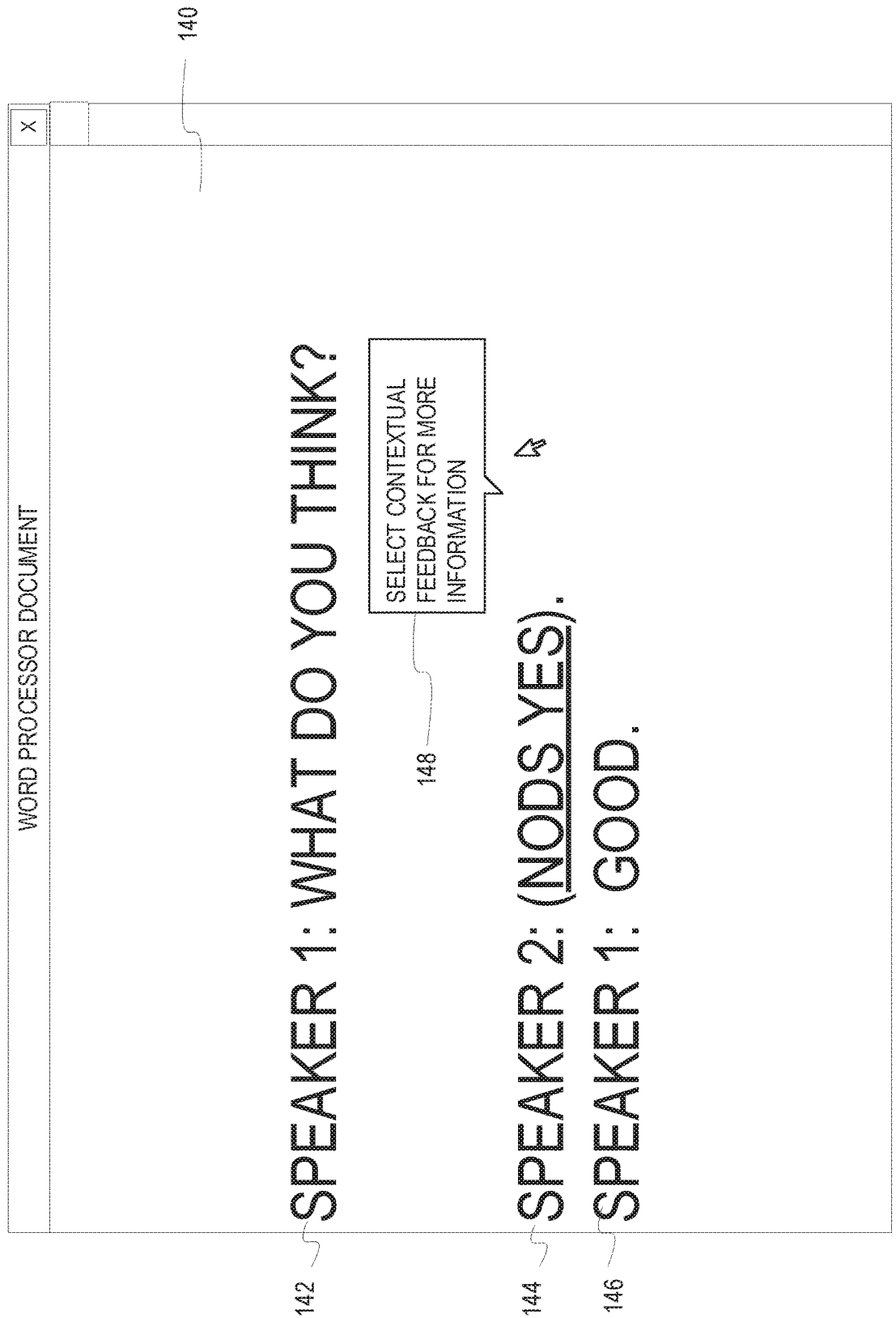
FIG. 7 illustrates one example of a screen display for a software application where contextual feedback is sensed by the earpiece and received into the software application.

FIG. 7 illustrates another example of a screen display 140. As shown in FIG. 7, a transcript may be created which includes text from multiple different speakers. As shown, each speaker may be identified such as "Speaker 1", "Speaker 2." Alternatively, each speaker may be given a name. In addition to a transcript of text, the ear piece may include other information sensed by the ear piece. For example, where the ear piece includes an inertial sensor, information associated with the inertial sensor or a characterization of information associated with the inertial sensor may be included. In this example, "Speaker 2" is wearing the earpiece. The statement 142 made by Speaker 1 may be detected with an externally facing microphone of an earpiece worn by Speaker 2. In response to statement 142, Speaker 2 may nod their head in agreement. This gesture or movement associated with the head nod may be detected with one or more inertial sensors of the earpiece. This head movement or a record of it may then be incorporated into the transcript. The record of the head movement 146 may be shown in a manner distinct from the voice transcript such as using different colors, fonts, or styles, such as underlining, including in parentheses, or otherwise. In addition, additional information may be obtained by selecting the inserted text indicating that the nod occurred. The additional information may be in the form of raw sensor data, or other characterization of the nod or other sensor data. Examples of different characterizations may include the degree of the head nod or characterization of how pronounced the head nod is. The characterizations may be quantitative or qualitative. A tooltip 148 may be shown indicating that a user may select the contextual feedback to access this additional information. In addition to head nods, other gestures may also be detected. This may include a head shaking movement, such as may be associated with a "NO." Although gestures as detected with inertial sensors are one type of movement which may detected to provide contextual feedback, it is contemplated that other types of contextual feedback may be used such as may be detected through physiological monitoring or otherwise. Other types of sensors may also include image sensors. Where image sensors are used, the image sensors may be used to detect information from either the individual wearing the earpiece or other wearable device or from others. Thus, records may be created for nonverbal information as a part of a transcript of a communication or as input into different fields within a document or software application.

In another embodiment, a person is using the earpieces on a phone call and the voice of the person on the other side of the call is captured and transcribed as opposed to capturing voice of a person through one or more microphones on the ear piece. In yet another embodiment, a conversation may occur either in person or over a communication network with two or more individuals with at least two of the individuals wearing earpieces so that contextual information from more than one person may be captured as a part of the conversation.

Therefore, methods and systems for voice dictation using one or more earpieces have been shown and described. Although specific embodiments are shown here, it is contemplated that any number of options, variations, and alternatives may also be used. The present invention is not to be limited unduly to specifically what is shown and described herein.

What is claimed is:

1. A system for voice dictation, the system comprising:
an earpiece, the earpiece comprising:
an earpiece housing sized to fit into an external auditory canal of a user;
a first microphone operatively connected to the earpiece housing and positioned to be isolated from ambient sound when the earpiece housing is fitted into the external auditory canal;
a second microphone operatively connected to the earpiece housing and positioned to detect sound external from the user;
a processor disposed within the earpiece housing and operatively connected to the first microphone and the second microphone and an inertial sensor, wherein the processor is adapted to capture a first voice audio stream using at least the first microphone, the first voice audio stream associated with the user, and a second voice audio stream using at least the second microphone, the second voice audio stream associated with a person other than the user, and wherein the processor is configured to interpret input from the inertial sensor as a head movement;
a computing device executing a software application to receive the first voice audio stream into a first position of a record and to receive the second voice audio stream into a second position of the record, wherein the computing device executing the software application is configured to allow for review of the first audio stream, wherein the computing device executing the software application is further configured to identify the user and the person other than the user;
wherein the computing device is configured to execute the software application to indicate occurrence of the head movement by the user at a third position of the record.

2. The system of claim 1, wherein the record is a medical record, the user is a health care provider and the person other than the user is a patient.

3. The system of claim 2, wherein the computing device is configured to execute the software application to convert the first voice audio stream into a first audio file, store the first audio file, convert the first voice audio stream into a first text and place both the first text and a first link to the first audio file at the first position of the record.

4. The system of claim 3, wherein the computing device is configured to execute the software application to convert the second voice audio stream into a second audio file, store the second audio file, convert the second voice audio stream into a second text and place both the second text and a second link to the second audio file at the second position of the record.

5. The system of claim 3, wherein the computing device is configured to execute the software application to edit the first text.

6. The system of claim 4, wherein the computing device is configured to execute the software application provides to edit the second text.

7. A system for voice dictation, the system comprising:
an earpiece, the earpiece comprising:
an earpiece housing sized to fit into an external auditory canal of a user and block the external auditory canal;
a first microphone operatively connected to the earpiece housing and positioned to be isolated from ambient sound when the earpiece housing is fitted into the external auditory canal;
a second microphone operatively connected to the earpiece housing and positioned to detect sound external from the user;
an inertial sensor disposed within the earpiece housing;
a processor disposed within the earpiece housing and operatively connected to the inertial sensor, the first microphone and the second microphone, wherein the processor is adapted to capture a first voice audio stream using at least the first microphone, the first voice audio stream associated with the user, and a second voice audio stream using at least the second microphone, the second voice audio stream associated with a person other than the user, and wherein the processor is configured to interpret input from the inertial sensor as a head movement;
a computing device executing a software application to receive the first voice audio stream into a first position of a record and to receive the second voice audio stream into a second position of the record, wherein the computing device is configured to execute the software application to convert the first voice audio stream into a first audio file, store the first audio file, convert the first voice audio stream into first text and place both the first text and a first link to the first audio file at the first position of the record, wherein the computing device executing the software application is further configured to allow for review and modification of the first text, wherein the computing device executing the software application is further configured to identify the user and the person other than the user;
wherein the computing device is configured to execute the software application to indicate occurrence of the head movement by the user at a third position of the record.

8. The system of claim 7, wherein the record is a medical record, the user is a health care provider and the person other than the user is a patient.

9. The system of claim 7, wherein the computing device is further configured to execute the software application provides to convert the second voice audio stream into a second audio file, store the second audio file, convert the second voice audio stream into second text and place both the second text and a second link to the second audio file at the second position of the record.

10. The system of claim 9, wherein the computing device is further configured to execute the software application to provide for editing the first text.

11. The system of claim 10, wherein the computing device is further configured to execute the software application provides to edit the second text.

12. The system of claim 9, wherein the user can insert a third text within a third position in the record, the third text coming from a captured third voice audio stream using at least the first microphone, the third voice audio stream associated with the user and converted into the third text.

* * * * *